United States Patent [19]

Kageyama et al.

[11] Patent Number: 4,916,059
[45] Date of Patent: Apr. 10, 1990

[54] REAGENT SHEET AND INTEGRAL MULTILAYER ANALYTICAL ELEMENT FOR MEASUREMENT OF GGT ACTIVITY

[75] Inventors: Shigeki Kageyama; Harumi Katsuyama, both of Asaka, Japan

[73] Assignee: Fuji Photo Film Co., Ltd., Kanagawa, Japan

[21] Appl. No.: 876,975

[22] Filed: Jun. 20, 1986

[30] Foreign Application Priority Data

Jun. 20, 1985 [JP] Japan .................. 60-135529
Jun. 20, 1985 [JP] Japan .................. 60-135530

[51] Int. Cl.$^4$ .................. C12Q 1/48
[52] U.S. Cl. .................. 435/15; 435/288
[58] Field of Search .................. 435/15

[56] References Cited

U.S. PATENT DOCUMENTS

| | | | |
|---|---|---|---|
| 3,891,507 | 6/1975 | Breuer | 435/16 |
| 4,087,331 | 5/1978 | Bucolo et al. | 435/110 |
| 4,372,874 | 2/1983 | Modrovich | 435/15 |
| 4,603,107 | 7/1986 | Deneke et al. | 435/15 |

OTHER PUBLICATIONS

Konishiroku–Chem. Abst., vol. 100 (1984) p. 47792h.

*Primary Examiner*—Sam Rosen
*Attorney, Agent, or Firm*—Jules E. Goldberg

[57] ABSTRACT

A reagent sheet for the measurement of GGT ($\gamma$-glutamyl transferase) activity comprising a porous sheet containing a cationic surfactant and a self-developable substrate upon contact with $\gamma$-glutamyl transferase. An integral multilayer analytical element for the measurement of GGT activity, comprising a porous spreading layer containing a cationic surfactant and a self-developable substrate in response to contact with $\gamma$-glutamyl transferase, a water-absorbing layer and a support in a laminated form. The substrate can be either $\gamma$-glutamyl-p-nitroamilide or $\gamma$-glutamyl-3-carboxy-4-nitroamilide.

15 Claims, 1 Drawing Sheet

F I G. 1
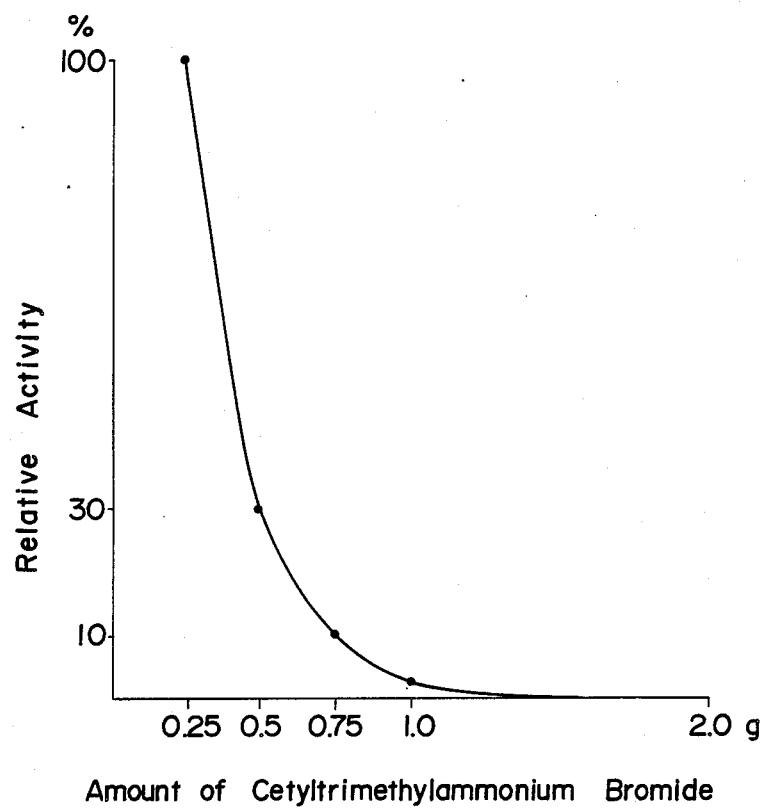

REAGENT SHEET AND INTEGRAL MULTILAYER ANALYTICAL ELEMENT FOR MEASUREMENT OF GGT ACTIVITY

BACKGROUND OF THE INVENTION

1. Field of the Invention

The present invention relates to a reagent sheet for use in the measurement of γ-glutamyl transferase activity in a liquid sample and an integral multilayer analytical element for use in the measurement of said activity, and more particularly to a reagent sheet and an integral multilayer analytical element for use in the analysis of aqueous sample solutions, particularly in the analysis of γ-glutamyl transferase activity in body fluids in clinical test.

2. Description of Prior Arts

It is very important to measure the activity of γ-glutamyl transferase in human body fluids in clinical test. As enzyme activity relating to a cancer of the liver, bile duct or the pancreas, there is frequently done the measurement of the activity of γ-glutamyl transferase (hereinafter referred to sometimes as GGT) in body fluids in the diagnosis of said cancer.

As the method of measurement of GGT activity, there had been reported a GGT activity measuring method using a synthetic substrate by A. Szewczuk M. Orlowski in 1960 [see, Clin. Chem. Acta, 5; 680–688, (1980)]. Since then, various synthetic compounds for the measurement of GGT activity had been synthesized, systems of conjugation reactions with color-forming reactions had been developed, and various methods are widely used at the present time [see, Japanese Patent Provisional Publication Nos. 54(1979)-133191, 53(1978)-111793, 54(1979)-132533, 56(1981)-148298, 56(1981)-148299, 56(1981)-164796, 56(1981)-23897, 56(1981)-92845, 56(1981)-158745, 56(1981)-169597, 56(1981)-30956, 53(1978)-147034, 54(1979)-28195 and 55(1980)-26870].

Most of the aforementioned methods use consecutive reactions in which pH of the reaction system is changed to form a color or there is added a color reagent which has a fear of said reagent itself or an intermediate inhibiting an enzyme reaction. Though there are only a few cases at present, there are synthesized some substrates which allows the enzyme reaction itself to be directly observed, that is, some self-developable substrates having velocity method applicability.

As the self-developable substrates for the measurement of GGT activity, there are known γ-glutamyl-p-nitroanilide developed by M. Orlowski [see, Arch. Immunol. Ther. Exp., 13, 538 (1985)] and γ-glutamyl-3-carboxy-4-nitroanilide disclosed in Japanese Patent Publication No. 54(1979-7781.

The latter is superior in solubility and used as a substrate for IFCC standard method. Although the former is poor in solubility, it has been early developed and its manufacturing cost is low, so that the substrate has been most studied, its clinical knowledge is rich, and it is widely used presently. In an analytical method using γ-glutamyl-p-nitroanilide as self-developable substrate, there is used a surfactant for dissolving said γ-glutamyl-p-nitroanilide which is difficultly soluble. However, it is known that the use of a cationic or anionic surfactant alone inhibits GGT activity. Thus, in conventional analytical methods, there is a serious problem how to dissolve γ-glutamyl-p-nitroanilide without inhibiting GGT activity.

As a method for dissolving γ-glutamyl-p-nitroanilide without inhibiting GGT activity, there is disclosed in Japanese Patent Publication No. 57(1982)-24759 a method in which γ-glutamyl-p-nitroanilide is dissolved in an aqueous solution containing both a cationic surfactant and a nonionic surfactant. Further, Japanese Patent Provisional Publication No. 55(1980)-153600 discloses a freeze-dried agent which can be almost instantaneously dissolved in a buffered test solution at 20° to 25° C. by adding a stoichiometric or excess amount of anionic surfactant to a base equal amount of γ-glutamyl-p-nitroanilide to form a protonized substrate and freeze-drying it. Conventional analytical methods including the above-described methods are those which are a so-called wet analytical method in which an analyte reacts with a reagent in a diluted aqueous solution.

An analytical method which can be performed with only a small amount of a sample and can be easily operated with high accuracy, has been highly desired by medical persons such as medical doctors in clinical test. Therefore, GGT activity-measuring methods using a dry analytical method in place of said conventional wet analytical method have been developed in recent years. In the dry analytical methods, reagents required for detection reaction are preserved in a dry state and the reaction of these reagents with a small quantity of a sample solution is detected to make the measurement. Among the dry analytical methods, there have been developed analytical methods using an integral multilayer analytical element which is easy to handle and the improvements of the element are being made. The integral multilayer analytical element for the measurement of GGT activity comprises a porous spreading layer containing a substrate which is self-developable in response to contact with γ-glutamyl-p-nitroanilide, a support layer and optionally other intervening functional layers such as a water-absorbing layer prepared by laminating them for integration.

The dry analytical methods using such an integral multilayer analytical element was reported by H. G. Curme, et al. [Clim. Chem., 24, 1335–1350 (1978) and B. Walter [Analytical Chemistry, (1983) 55, 493A].

However, when the activity of γ-glutamyl transferase is measured by these wet analytical methods, there are caused other problems in addition to those associated with the conventional wet analytical methods in which γ-glutamyl-p-nitroanilide is poor in solubility and the surfactants inhibits GGT activity. Unlike the wet analytical method, the substrate and other reagents are preserved in dry state in the dry analytical method. Therefore, when the substrate preserved in a dry state is brought into contact with a small amount of water in a liquid sample, the substrate must be readily re-dissolved in order to improve the accuracy of the measurement of GGT activity and to make the measurement over a wide range.

SUMMARY OF THE INVENTION

The present inventors have made studies in the measurement of γ-glutamyl transferase activity by the dry analytical method and have now surprisingly found that the cationic surfactant hardly inhibits GGT activity in the dry analytical method, even when the surfactant is used at a concentration at which the surfactant inhibits GGT activity in the conventional wet analytical method.

It is an object of the present invention to provide a reagent sheet for the measurement of GGT activity and an integral multilayer analytical element for the measurement of GGT activity which are free from the problems associated with the measurement of the activity of γ-glutamyl transferase in the conventional dry analytical method.

It is another object of the present invention to provide a reagent sheet and an integral multilayer analytical element for the measurement of GGT activity, which are easy to handle, can be readily operated and makes it possible to easily of Y-glutamyl unskilled persons such as medical doctors and nurses in clinical test.

Accordingly, the present invention provides in one aspect a reagent sheet for use in the measurement of the activity of γ-glutamyl transferase, which comprises a porous sheet containing a substrate which is sensitive to γ-glutamyl transferase and self-developable thereby, and a cationic surfactant in an amount in the range of 0.2 to 5 g./m².

The present invention provides in another aspect an integral multilayer analytical element for use in the measurement of the activity of γ-glutamyl transferase, which comprises a porous spreading layer containing a substrate, which is sensitive to γ-glutamyl transferase and self-developable thereby, and a cationic surfactant in an amount in the range of 0.2 to 5 g./m², a water-absorbing layer and a support layer in a laminated form.

In the reagent sheet and the integral multilayer analytical element for the measurement of the activity of γ-glutamyl transferase according to the present invention, the reagent sheet or the porous spreading layer (hereinafter referred to as spreading layer) of the element contains a self-developable substrate as well as a cationic surfactant in an amount in the range of 0.2 to 5 g./m². The cationic surfactant has an effect of stably dispersing the self-developable substrate in the reagent sheet or the spreading layer and uniformly containing it in an amorphous state with a high dissolving rate. Further, the cationic surfactant has an effect of improving the spreadability of a sample on the reagent sheet or the spreading layer.

The range of 0.2 to 5 g./m² for the cationic surfactant content of the reagent sheet or the spreading layer is a range within which the cationic surfactant functions effectively and does substantially not inhibit GGT activity. When in the conventional wet analytical method the cationic surfactant is used in such an amount that it functions effectively, it inhibits GGT activity to such an extent that the accuracy of the measurement is seriously affected, while in the dry analytical method using the reagent sheet and the integral multilayer analytical element of the invention, said cationic surfactant functions effectively and substantially does not inhibit GGT activity without requiring any other particular means.

The above unique structure of the reagent sheet or the spreading layer makes it possible that the reagent sheet and the integral multilayer analytical element for the measurement of the activity of γ-glutamyl transferase according to the invention are allowed to conduct measurement over a wide range and can be easily operated with high accuracy.

BRIEF DESCRIPTION OF THE DRAWINGS

FIG. 1 is a graph showing the correlation between the amount of cetyltrimethylammonium bromide used in the Comparison Example and the value of the relative activity of GGT measured in the solution method.

The values of the relative activity shown in FIG. 1 are calculated by taking as 100 the value of the relative activity where the amount of cetyltrimethylammonium bromide is 0.25 g.

DETAILED DESCRIPTION OF THE INVENTION

The porous reagent sheet for the measurement of the activity of γ-glutamyl transferase and the porous spreading layer of the integral multilayer analytical element for the measurement of said activity according to the invention have preferably a metering effect (i.e., metering the spotted liquid sample). The term "reagent sheet and spreading layer capable of metering a liquid sample" herein used refers to a layer having a function capable of spreading an applied liquid in such a manner that the spread area of the liquid is approximately in proportion to the amount of the liquid when the liquid is applied thereon. When the layer is spreading layer, it also has a function capable of supplying an uniform quantity of the liquid per area to a water-absorbing layer described hereinafter. Further, the reagent sheet and the spreading layer of the present invention preferably have spaces which allow γ-glutamyl transferase as an analyte to pass therethrough.

Therefore, it is preferred to use filter paper, woven fabric, nonwoven fabric, knitted fabric, glass fiber filter, membrane filter or a three-dimensional lattice structure composed of a polymer microbead as a material constituting a matrix of the reagent sheet or the spreading layer of the analytical element of the present invention.

Examples of the woven fabrics (woven cloth) which can be used for the reagent sheet or the spreading layer include those disclosed in Japanese Patent Provisional Publications No. 55(1980)-164356 and No. 57(1982)-66359. Among the woven fabrics, plain weave fabrics made of warp and weft are preferred. Among plain woven fabrics, thin cloth, muslin, broadcloth and poplin are preferred.

Examples of yarns for woven cloth include those composed of the same materials as those constituting knitted cloths as described in more detail hereinafter. Any of filament yard and spun yard (twist yarn) can be used, and the spun yard is preferred. The yard diameter of the woven fabric is generally in the range of about 20S to about 150S, preferably about 40S to about 120S in terms of cotton spinning yarn count or in the range of about 35 to about 300D, preferably about 45 to about 130D in terms of silk thread denier. The thickness of the woven fabric is generally in the range of about 100 to about 500 μm, preferably about 120 to 350 μm. The voids of the woven fabric are generally in the range of about 40 to about 90%, preferably about 50 to about 85%.

Examples of the knitted fabrics which can be used for the reagent sheet or the spreading layer include many kinds of knitted fabrics, among which warp knitted fabric and weft knitted fabric are preferred. Examples of the warp knitted fabrics include single atlas knitted cloth, tricot knitted cloth, double tricot knitted cloth, milanese knitted cloth and rashar knitted cloth. Examples of the weft knitted fabrics include plain weave knitted cloth, pearl knitted cloth, rib stitch cloth, and double face knitted cloth. Examples of the yarns for knitted fabrics include yarns of natural fibers such as cotton, silk and wool; yarns composed of fine fibers or single fibers of regenerated cellulose (e.g. viscose rayon and cupra), semi-synthetic organic polymer (e.g. cellulose diacetate and cellulose triacetate), synthetic organic polymer (e.g., polyamide such as nylon, acetalated polyvinyl alcohol such as vinylon, polyacrylonitrile, polyethylene terephthalate, polyethylene, polypropylene and polyurethane), and yarns composed of fiber blends of a natural fiber and a regenerated cellulose or a semi-synthetic or synthetic organic polymer fiber. Any of filament yarn and spun yard can be used, and spun yarn is preferred. The diameter of the yarn for knitted fabric is generally in the range of from about 40 to 150S, preferably about 60 to about 120S in terms of cotton spinning yarn count, or in the range of about 35 to about 130D, preferably about 45 to about 90D in terms of silk thread denier. The number of knitting gauge of the knitted fabric is generally in the range of about 20 to about 50. The thickness of the knitted fabric is generally in the range of about 100 to about 600 μm, preferably about 150 to about 400 μm. The voids of the knitted fabric are generally in the range of about 40 to about 90%, preferably about 50 to about 85%. The warp knitted fabric, tricot knitted cloth, rashar knitted cloth, milanese knitted cloth and double tricot knitted cloth are preferred, because shrinkage in the wale's direction is small, the operation in the lamination stage of knitted goods is easy and the stitches are not easily loosened during cutting.

Woven fabric or knitted fabric is preferably a fabric from which fat is substantially removed when the yarn or the fabric is prepared. The fabrics are more preferably processed to be hydrophilic to enhance the adhesion to an underlying layer, when the fabric is used as the spreading layer. Examples of such process to make the fabric hydrophilic include physical activating process (preferably glow discharge process or corona discharge process) disclosed in Japanese Patent Provisional Publication No. 57(1982)-66359 and hydrophilic polymer permeating process disclosed in Japanese Patent Provisional Publication Nos. 55(1980)-164356 and 57(1982)-66359.

The spreading layer constituted of woven fabric or knitted fabric can be laminated on a water-adsorbing layer or adhesive layer according to the process disclosed in Japanese Patent Provisional Publications No. 55(1980)-164356 and No. 57(1982)-66359. The process is that woven fabric or knitted fabric is laminated under the substantially uniform light pressure on the wet or swelling buffer layer or adhesive layer which has been still wet condition after coating or has been supplied with water (or water containing small amount of detergent) after drying).

The reagent sheet or the spreading layer constituted of a brush polymer or a membrane filter can be provided according to the process disclosed in Japanese Patent Publication No. 53(1978)-21677, the reagent sheet or the spreading layer having a three-dimensional lattice structure constituted of polymer microbead can be provided according to the method disclosed in Japanese Patent Provisional Publication No. 55(1980)-90859, and the reagent sheet or the spreading layer constituted of filter paper or nonwoven fabric can be provided according to the process disclosed in Japanese Patent Provisional Publication No. 57(1982)-148250.

When a water-absorbing layer or an adhesive layer described hereinafter is made of gelatin or gelatin derivatives, the spreading layer made of woven fabric or knitted fabric is preferably laminated on the wet or swelling gelatin (or its derivatives) of water-absorbing layer or adhesive layer which has been still wet condition after coating.

The reagent sheet of the present invention contains a self-developable substrate. In the integral multilayer analytical element of the present invention, the spreading layer contains a self-developable reagent. The term "self-developable substrate" used herein refers to a substance which serves as a substrate for γ-glutamyl group-transferase and undergoes a γ-glutamyl group-transferring reaction to thereby form a detectable color or produce a detectable color change. Examples of the self-developable substrates include γ-glutamyl-p-nitroanilide and γ-glutamyl-3-carboxy-4-nitroanilide. In the present invention, γ-glutamyl-p-nitroanilide is particularly preferred as the substrate.

The reagent sheet for the measurement of the activity of γ-glutamyl transferase contains a cationic surfactant. In the integral multilayer analytical element for the measurement of the activity, the spreading layer contains a cationic surfactant. Any of cationic surfactants may be used in the invention without specific limitation. However, quaternary ammonium salt type cationic surfactants are preferred. Examples of such quaternary ammonium salt type cationic surfactants include those having the following formula:

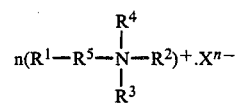

wherein n is 1 or 2; $R^1$ is an alkyl group having 12 or more carbon atoms; $R^2$, $R^3$ and $R^4$ are the same or different from each other, and each is methyl, ethyl or benzyl group, or $R^2$, $R^3$ and $R^4$ may form a piperidinium group together with the neighboring nitrogen atom; $R^5$ is a single bond or a group of —$CONHR^6$— (wherein $R^6$ is methylene or ethylene group); and X is halogen ion, sulfate ion or methanesulfonate ion.

Examples of the surfactants having the above formula where $R^5$ is a single bond, include laurytrimethylammonium chloride, stearyltrimethylammonium bromide, cetyltrimethylammonium chloride, laurytrimethylammonium sulfate, cetyldimethylbenzylammonium bromide, lauryldimethylbenzylammonium chloride, myristyldimethylbenzylammonium chloride, cetylpyridinium bromide and laurylpyridinium chloride.

Other examples of the surfactants having the above formula where $R^5$ is —$CONHR^6$— include stearamidomethylpyridinium chloride and those which are commercially available under the trade name of Sapamine MS, Sapamine BCH and Caternack SN.

Said cationic surfactant in the range of 0.2 to 5 g./m², preferably about 0.5 to about 3 g./m² is incorporated in the reagent sheet or the spreading layer of the analytical element of the present invention.

If desired, the reagent sheet and the spreading layer of the analytical element of the present invention may contain a nonionic surfactant, a hydrophilic polymer, reagents such as enzyme activator and buffering agent, fine light-blocking particles, etc. in addition to said self-developable substrate and said cationic surfactant.

Any of nonionic surfactants may be used in the present invention without particular limitation. However, nonionic surfactants having HLB value [Hydrophile-Lipophile-Balance; according to the definition of J. Soc. Cosmet. Chem., 1,311 (1949) or "Kagaku" 23,546

(1953)] of 10 or more are preferred. The nonionic surfactant having the HLB value may be selected from ethylene oxide adducts (i.e., condensation products) of polyhydric alcohol ester, polyethylene glycol monoester, polyethylene glycol diester, ethylene oxide adducts (condensation products) of higher alcohol, ethylene oxide adducts (condensation products) of alkylphenol, and alkanol amides of higher fatty acid.

A combination of two or more surfactants may be used as the nonionic surfactant. HLB value of the surfactant can be adjusted by using said combination of the surfactants (including surfactants having HLB value of less than 10).

Examples of the nonionic surfactant having HLB value of 10 or more and their HLB values are described in the following Table 1.

TABLE 1 (1)

| Nonionic Surfactant | HLB value |
|---|---|
| POE (20) sorbitan monooleate | 15.0 |
| POE (10) sorbitan monooleate | 13.5 |
| POE (4) sorbitan tristearate | 10.5 |
| POE (4) trioleate | 11.0 |
| POE (30) stearate | 16.0 |
| POE (40) stearate | 16.9 |
| POE (100) stearate | 18.8 |
| PEG (400) monostearate | 11.6 |
| PEG (400) monolaurate | 13.1 |
| PEG (1000) dilaurate | 14.1 |
| PEG (1540) distearate | 14.8 |
| Condensation product of lauryl alcohol and 6 mol. of EO | 11.8 |
| Condensation product of lauryl alcohol and 10 mol. of EO | 14.1 |
| Condensation product of lauryl alcohol and 30 mol. of EO | 17.4 |
| Condensation product of lauryl alcohol and 20 mol. of EO | 15.3 |
| Condensation product of cetyl alcohol and 20 mol. of EO | 15.7 |

TABLE 1 (2)

| Nonionic Surfactant | HLB value |
|---|---|
| POE (9–10) octyl phenyl ether | 13.5 |
| POE (15) octyl phenyl ether | 15.1 |
| POE (30) octyl phenyl ether | 17.4 |
| POE (40) octyl phenyl ether | 18.7 |
| POE (10) nonyl phenyl ether | 11.7 |
| POE (12) nonyl phenyl ether | 14.1 |
| POE (20) nonyl phenyl ether | 16.0 |
| POE (50) nonyl phenyl ether | 19.5 |
| Triethanolamine oleate | 12.0 |

In the Tabel 1, POE is polyethylene oxide, PEG is polyethylene glycol, EO is ethylene oxide, and the numbers in parentheses are condensation numbers of ethylene oxide units.

Said nonionic surfactant preferably in an amount in the range of about 0.1 to about 3 g./m$^2$, more preferably about 0.2 to about 2 g./m$^2$ is incorporated in the reagent sheet or the spreading layer of the analytical element of the present invention.

Said nonionic surfactant (particularly surfactant having HLB value of 10 or more) has an effect of improving the spreadability of a sample on the reagent sheet or the spreading layer.

Examples of the hydrophilic polymers which can be incorporated in the reagent sheet or the spreading layer of the analytical element of the invention include starch, cellulose, agarose, gelatin and their derivatives (e.g., hydroxymethylated and hydroxypropylated derivatives), acrylamide polymer, copolymers of acrylamide with other vinyl monomer, vinylpyrrolidone polymer, copolymers of vinylpyrrolidone with other vinyl monomer, acrylate polymer, and copolymers of an acrylate with other vinyl monomer. Among them, acrylamide polymer and cellulose derivatives are preferred.

Particularly preferred examples of the cellulose derivatives are cellulose ethers where part of the whole of hydroxyl groups is etherified with an alkyl group having 1 to 3 carbon atoms or a hydroxyl group-substituted lower alkyl group having 1 to 4 carbon atoms. Examples of such cellulose ethers include methylcellulose, ethylcellulose, hydroxyethylcellulose, hydroxypropylcellulose and hydroxybutylmethylcellulose.

The hydrophilic polymer in an amount in the range of about 0.5 to 15 g./m$^2$, preferably about 2 to 10 g./m$^2$ is incorporated in the reagent sheet or the spreading layer of the analytical element of the present invention.

Said hydrophilic polymer has an effect of preserving small amount of water in the spotted sample to accelerate the catalytic reaction of analyte enzyme.

The enzyme activators which can be incorporated in the reagent sheet or the spreading layer of the analytical element of the present invention are those serving as an acceptor for γ-glutamyl groups to be transferred from the substrate by the action of γ-glutamyl transferase. Examples of such γ-glutamyl group acceptors include various amino acids and oligopeptides. However, when a sufficient amount of such component serving as an acceptor is contained in a sample solution, it is not necessary to incorporate such an acceptor in the reagent sheet or the spreading layer.

Such γ-glutamyl group acceptors are described in literature such as Clinical Chemistry, Vol. 24, No. 6 (1978) 905–915 by L. M. Shaw. Preferred examples of the γ-glutamyl group acceptors include D-methionine, L-methionine, L-glutamine, L-leucine, L-alanine, L-lysine, L-cysteine, glycyglycine and glycylglycygly-cine, among which glycylglycine is particularly preferred.

Examples of light-blocking and light-reflecting particles which can be incorporated in the reagent layer of the spreading layer of the analytical element of the present invention include titanium dioxide fine particles (rutile-type, anatase-type or brookite-type; mean size ranging from approx. 0.1 μm to approx. 1.2 μm), barium sulfate fine particles, aluminum fine particles and fine flakes thereof. Examples of light-blocking particles include carbon black, gas black and carbon microbeads. Titanium dioxide fine particles and barium sulfate fine particles are preferred and anatase-type titanium dioxide fine particle is most preferred.

The self-developable substrate, the cationic surfactant, the nonionic surfactant, the hydrophilic polymer, the reagents such as enzyme activator and the buffering agent and the fine light-blocking particle can be incorporated in the reagent sheet or the spreading layer by spraying a coating solution containing said ingredients over the reagent sheet or the spreading layer and drying it.

When the reagent sheet or the spraying layer is composed of woven fabric, knitted fabric, filter paper, nonwoven fabric or glass fiber filter paper, the reagent sheet or the spreading layer is immersed in a solution containing said ingredients and dried. When the spreading layer is composed of materials to be laminated, the materials are immersed in said solution and are laminated in a dry or semi-dry state on each other for integration.

When the spreading layer is to be formed by coating, for instance, the spreading layer is composed of a brush polymer layer or a three-dimensional lattice microbead structure, a mixture of a coating solution for the spreading layer and a coating solution containing said ingredients may be coated.

These ingredients can be incorporated in the reagent sheet or the spreading layer by using different methods for every ingredient, or by applying separately every ingredient. However, it is desirable that a solution containing both the self-developable substrate (particularly γ-glutamyl-p-nitroanilide) and the cationic surfactant is prepared, so that the cationic surfactant sufficiently reacts with the substrate.

The material of the support of the analytical element of the invention is preferably a light-transmissive, liquid-impermeable support.

Examples of the liquid-impermeable, light-transmissive supports include substantially water-impermeable transparent supports in the form of a film or sheet made of a polymer such as polyethylene terephthalate, polycarbonate of bisphenol A, polystyrene and cellulose esters (e.g., cellulose diacetate, cellulose triacetete, cellulose acetate propionate etc.). The thickness of the support generally ranges from approx. 50 μm to approx. 1 mm, preferably from approx. 80 μm to approx. 300 μm.

The reagent sheet for the measurement of the activity of γ-glutamyl transferase according to the present invention can be laminated onto the support to integrate them. The support to be laminated onto the reagent sheet is preferably a support which does not transmit light or contains a light-reflecting colorant. Such a light-nontransmitting support or a light reflecting colorant-containing support can be easily prepared by incorporating a light-reflecting colorant in said polymer, by coating the surface of a transparent support composed of said polymer with a light-reflecting colorant, or by sticking a pressure-sensitive adhesive tape containing a light-reflecting colorant on a support.

There may be provided an undercoating layer on the support to enhance the adhesion between the support and a water-absorbing layer or the reagent sheet. Instead of providing the undercoating layer, the surface of the support may be activated by a physical or chemical process to enhance the adhesion.

There is provided a water-absorbing layer on the support (optionally, intervened by other layers such as undercoating layer). The water-absorbing layer is a layer comprising a hydrophilic binder which is preferably a hydrophilic polymer which absorbs water to swell.

The hydrophilic polymer preferably shows swelling ratio ranging from approx. 150% to approx. 2,000%, more preferably from approx. 250% to approx. 1,500% at 30° C. Examples of the hydrophilic polymer satisfying the above-described conditions include gelatin (e.g., acid-processed gelatin, deionized gelatin etc.), gelatin derivatives (e.g., phthalated gelatin, hydroxyacrylate grafted gelatin etc.), agarose, pullulan, pullulan derivatives, dextran, polyacrylamide, polyvinyl alcohol, and polyvinyl pyrrolidone.

The dry thickness of the water-absorbing layer is in the range of about 1 to 100 μm, preferably about 3 to 30 μm. Preferably, the water-absorbing layer should be substantially transparent.

If desired, a buffering agent may be incorporated in the water-absorbing layer. Examples of such buffering agents include conventional buffering agents such as carbonates, borates, phosphates and good's buffering agents. These buffering agents can be chosen by referring to literatures such as "Fundamental Experimental Method of Protein.Enzyme" by T. Horio et al. (Nankodo, 1981) written in Japanese.

There may be provided a light-blocking layer on the water-absorbing layer. The light-blocking layer is a water-permeable layer in which light-blocking (or light-reflecting) fine particles are dispersed in small amount of a film-forming hydrophilic polymer binder. The light-blocking layer may function as light-reflecting layer or background layer as well as blocker to the color of an aqueous liquid spotted on the spreading layer, such as the red of hemoglobin in a whole blood sample, when a detectable change (a color change or a color development etc.) in the water-absorbing layer is measured from the side of the transparent support reflection photometry.

Examples of light-blocking and light-reflecting particle include fine titanium dioxide particles (rutile-type, anatase-type or brookite-type; mean size ranging from approx. 0.1 μm to approx. 1.2 μm), fine barium sulfate particles, fine aluminum particles and their flakes. Examples of light-blocking particles include carbon black, gas black and carbon microbeads. Fine titanium dioxide particles and fine barium sulfate particles are preferred, and anatase type titanium dioxide particles are most preferred.

Examples of the film-forming hydrophilic polymer binder include a weakly hydrophilic polymer such as regenerated cellulose and cellulose acetate as well as the hydrophilic polymer employable in the reactive layer. Most preferred are gelatin, gelatin derivatives and polyacrylamide. Gelatin and gelatin derivatives may be used as a mixture with a known hardening agent (cross-linking agent).

The light-blocking layer can be provided in such a manner than an aqueous dispersion containing the light-blocking particle and the hydrophilic polymer is coated on the reaction layer and then dried by any of the conventional methods. Instead of the light-blocking layer, the light-blocking particles may be incorporated into the spreading layer.

There may be provided an adhesive layer on the water-absorbing layer or optionally added other layer (e.g., light-blocking layer) to enhance the adhesion of the spreading layer.

The adhesive layer is preferably constituted by a hydrophilic polymer which can bond the spreading layer to other layer to make all of the layers integrated while the polymer is wetted or swelled with water. Examples of the hydrophilic polymer include the polymers employable in the water-absorbing layer. Most preferred are gelatin, gelatin derivatives and polyacrylamide. The dry thickness of the adhesive layer generally ranges from approx. 0.5 μm to approx. 20 μm, preferably from approx. 1 μm to approx. 10 μm.

The adhesive layer may be provided on other layers as well as the water-absorbing layer. The adhesive layer can be prepared in such a manner that a solution of a hydrophilic polymer and optionally added other agent such as a surfactant is coated on the water-absorbing layer or other layer.

The integral multilayer analytical element for the measurement of GGT activity according to the invention comprises a support, a water-absorbing layer and a spreading layer in the form of a laminate, and it is preferred that these layers are laminated in the above-described order. The analytical element of the present invention may optionally contain other functional layers in addition to the above-described essential layers.

The reagent sheet for the measurement of GGT activity according to the present invention is composed of a single sheet and if desired, the reagent sheet may be laminated onto a support.

It is preferred from the viewpoint of manufacture, packaging, transportation, preservation and measuring operation that the integral multilayer analytical element of the present invention is cut into pieces of about 15 to 30 mm square or a circle of about 15 to 30 mm in diameter and put in a slide frame to provide an analytical slide as disclosed in Japanese Patent Provisional Publication Nos. 57(1982)-63452 and 54(1979)-156079, Japanese Utility Model Provisional Publication Nos. 56(1981)-142454 and 58(1983)-32350 and Japanese Patent Provisional Publication No. 58(1983)-501144.

About 5 to about 30 μl, preferably about 8 to about 15 μl of an aqueous liquid sample is deposited (spotted) on the reagent sheet or the porous spreading layer of the integral multilayer analytical element of the invention, and if necessary, the reagent sheet or the analytical element is incubated at a substantially constant temperature of about 20° to 45° C. A detectable change such as color change or color formation in the sheet or the element is measured (from the side of the light-transmissive support when the analytical element is used) by reflection photometry to thereby analyze a substance to be measured in the liquid sample according to colormetry.

The following examples and comparison example are provided to illustrate the present invention without limiting it thereto.

EXAMPLE 1

The surface of a transparent polyethylene terephthalate support of 180 μm in thickness was treated to make it hydrophilic. The hydrophilic surface of the support was coated with the coating solution having the following composition and dried to form a water-absorbing layer of 15 μm in dry film thickness.

| Coating Solution for Water-absorbing Layer | |
|---|---|
| Alkali-treated deionized gelatin | 10 g. |
| Octylphenoxy polyethoxyethanol | 0.5 g. |
| Water | 100 ml |
| 1,2-Bis(vinylsulfonylacetamido)ethane | 0.15 g. |

The surface of said water-absorbing layer was coated with the coating solution having the following composition and dried to form an adhesive layer of 3 μm in dry film thickness.

| Coating Solution for Adhesive Layer | |
|---|---|
| Gelatin | 12 g. |
| Water | 290 g. |
| Nonylphenoxy polyglycidol | 1.3 g. |

The surface of said adhesive layer was wetted with a 0.4% aqueous solution of nonylphenoxy polyglycidol. A tricot fabric composed of a spun yarn of polyethylene terephthalate (36 gauge, 50 denier, about 230 μm thick) was laminated onto said wetted surface under pressure to form a spreading layer.

The following substrate coating solution was applied to the spreading layer in a coating amount of 120 ml/m² and dried.

Preparation of Substrate Coating Solution

A solution of 2.28 g. of γ-glutamyl-p-nitroanilide dissolved in a solution of 1 ml of 2N hydrochloric acid and 1 ml of ethanol was added to the following uniform solution, and pH of the resulting solution was adjusted to 8.3 by the addition of 1.3 ml of 6N hydrochloric acid to prepare the substrate coating solution.

| Uniform Solution | |
|---|---|
| Tris(hydroxyethyl)aminomethane | 3.03 g. |
| Glycylglycine | 0.651 g. |
| Cetyltrimethylammonium bromide | 0.500 g. |
| Water | 20.0 g. |
| Polyacrylamide (10 wt. % aqueous solution) (viscosity at 25° C.: 2500 cps.) | 25 g. |

The surface of the spreading layer was coated with the following titanium dioxide coating solution in a coating amount of 112 ml/m² and dried.

| Titanium Dioxide Coating Solution | |
|---|---|
| Anatase type titanium dioxide | 2.5 g. |
| 0.5% hydroxylethyl cellulose | 50 ml |

In this way, an integral multilayer analytical element (the cationic surfactant [cetyltrimethylammonium bromide] content of the spreading layer: about 1 g./m²) for the measurement of GGT activity according to the present invention was prepared.

EXAMPLE 2

The procedure of Example 1 was repeated except that the amount of cetyltrimethylammonium bromide used in the uniform solution was 0.250 g. in place of 0.50 g. to prepare an analytical element (cationic surfactant [cetyltrimethylammonium bromide] content of the spreading layer: about 0.5 g./m²) for the measurement of GGT activity according to the present invention.

EXAMPLE 3

The procedure of Example 1 was repeated except that the amount of cetyltrimethylammonium bromide used in the uniform solution was 1.0 g. in place of 0.50 g. to prepare an analytical element (cationic surfactant [cetyltrimethylammonium bromide] content of the spreading layer: about 2 g./m²) for the measurement of GGT activity according to the present invention.

Each of the analytical elements obtained by Examples 1 to 3 was cut into a piece 15 mm square and put in a plastic mount (disclosed in Japanese Patent Provisional Publication No. 57(1982)-63452) to prepare a slide for the analysis of GGT.

GGT of bovine kidney, which had a GGT activity of 1900 U/L from the measurement with RA 1000 (a wet-process analyzer) manufactured by Technicon Co. Ltd., was dissolved in commercial available control serum, and the resulting solution was added to each of the above slides.

The resulting control solution was used as a specimen. 10 μl of the control solution was applied (dropped) on each slide, the hole of the deposited side was closed by a pressure-sensitive adhesive tape (Mylar) to prevent water from being evaporated, each slide was heated on a 37° C. constant heated block, and the reflection density of each slide on the transparent support was measured with a light of 400 nm after 2 and 5 minutes, respectively. The results are shown in Table 2.

TABLE 2

| Analytical Slide | OD (5 min.–2 min.) |
|---|---|
| Example 1 | 0.223 |
| Example 2 | 0.230 |
| Example 3 | 0.222 |

It is apparent from the above results that there are no much fluctuations in GGT activity over a cetyltrimethylammonium bromide content range of 0.5 to 2 g./m².

COMPARISON EXAMPLE

The procedure of Example 1 was repeated except that polyacrylamide was omitted from the uniform solution and the amount of cetyltrimethylammonium bromide was 0.25 to 2.0 g. to prepare a uniform solution. In a similar manner to that described in Example 1, γ-glutamyl-p-nitroanilide was added to each of the uniform solutions to prepare a substrate solution. 30 μl of each substrate solution was put in a cuvette, 10 μl of the same control serum as that of Example 3 was added thereto, the cuvette was kept at 37° C. and the transmitted optical density thereof was measured with a light having a central wavelength of 410 nm. The relative activity value of GGT was determined from the resulting optical density. The results are shown in FIG. 1.

FIG. 1 is a graph showing the correlation between the amount of cetyltrimethylammonium bromide used in the Comparison Example and the value of the relative activity of GGT measured in the solution method.

The values of the relative activity shown in FIG. 1 are calculated by taking as 100 the value of a relative activity where the amount of cetyltrimethylammonium bromide is 0.25 g.

It is apparent from FIG. 1 that when the cetyltrimethylammonium bromide content is 0.5 g., the ratio of inhibition in the activity of GGT is 30%; when the content is 0.75 g., the ratio is 10%; and when the content is 1.0 g. or higher, cetyltrimethylammonium bromide inhibits the activity to such an extent that the measurement is practically impossible.

Therefore it is also apparent that even when cetyltrimethylammonium bromide is used in an amount which does almost not inhibit the activity in the dry analytical method of the present invention, such an amount is to cause a serious inhibition to the measurement in the solution method.

EXAMPLE 4

The analytical element was cut into pieces of 15 mm square and each was put into a plastic mount (disclosed in Japanese Patent Provisional Publication No. 57(1982)-63452) to prepare an analytical slide for the analysis of GGT.

While heating said slide on a 37° C. constant heated block, 10 μl of each of commercially available control serums containing bovine kidney GGT having GGT activity of 10, 150, 290, 600 and 1150 U/L was deposited (dropped) on the slide, and the color density thereof was measured with a light of 410 nm after 2 and 5 minutes, while preventing water from being evaporated.

The values of the color density were those calculated from a color density to p-nitroaniline conversion formula which was prepared by using an aqueous p-nitroaniline solution having a known concentration.

The measured and calculated results are shown in Table 3.

The values of Table 3 are calculated from the following formula:

$$Y = 1.5692 \times 10^{-3} X + 0.16853$$

wherein X is color density and Y is the concentration of p-nitroaniline.

TABLE 3

| GGT activity (U/L) | Amount of p-nitroaniline formed |
|---|---|
| 10 | 0.090 mM |
| 150 | 0.405 mM |
| 290 | 0.700 mM |
| 600 | 1.184 mM |
| 1150 | 1.916 mM |

The coefficient γ of correlation is 0.99425 from the results of Table 3. It is apparent from Table 3 that the slides having the analytical element of the invention produce p-nitroaniline in well correlation to GGT activity and hence, the analytical element of the present invention is effective in measuring GGT activity.

EXAMPLE 5

The procedure of Example 1 was repeated except that an equal amount of each of cationic surfactants given in Table 4 was used in place of cetyltrimethylammonium bromide used in the uniform solution to prepare an analytical element. Slides for the analysis of GGT were prepared therefrom, and it was found that any of the slides was effective in the measurement of GGT activity as in Example 4.

TABLE 4

| No. | Cationic Surfactant |
|---|---|
| 5-1 | cetyltrimethylammonium chloride |
| 5-2 | cetylpyridinium bromide |
| 5-3 | cetylpyridinium chloride |
| 5-4 | tetradecyldimethylbenzylammonium chloride |
| 5-5 | octadecyltrimethylammonium bromide |

EXAMPLE 6

A glass fiber filter of 200 μm in thickness was impregnated with the substrate coating solution of Example 1 in a coating amount of 100 ml/m², and cut into a 1 cm² sheet which was then fixed to a flat plastic plate containing a white pigment incorporated therein to obtain a reagent sheet for the measurement of GGT activity.

10 μl of serum was deposited on said reagent sheet. After 10 minutes, the reflection density was measured with Macbeth reflection densitometer and there was detected an yellow color density in proportion to the GGT activity of the deposited solution.

EXAMPLE 7

The procedure of Example 1 was repeated except that the following titanium dioxide coating solution was used in place of that used in Example 1 to prepare an analytical element (the spreading layer containing both cationic surfactant and nonionic surfactant) for the measurement of GGT activity according to the present invention.

| Titanium Dioxide Coating Solution | |
|---|---|
| Anatase type titanium dioxide | 2.5 g. |
| 0.5% hydroxylethyl cellulose | 50 ml |
| POE (50) nonyl phenyl ether (HLB value; 19.5) | 2.5 g. |

EXAMPLE 8

The procedure of Example 7 was repeated except that 50 ml of 0.5% hydroxylmethyl cellulose was used in place of 50 ml of 0.5% hydroxylethyl cellulose used in the titanium dioxide coating solution and each of nonionic surfactants given in Table 5 was used in place of POE(50) nonyl phenyl ether used in the titanium dioxide coating solution to prepare an analytical element.

TABLE 5

| No. | Nonionic Surfactant | (HLB value) | Content |
|---|---|---|---|
| 8-1 | POE (40) octyl phenyl ether | (18.7) | 2.5 g. |
| 8-2 | POE (50) nonyl phenyl ether | (19.5) | 2.0 g. |
| 8-3 | POE (9-10) octyl phenyl ether | (13.5) | 0.5 g. |
| 8-4 | POE (9-10) octyl phenyl ether | (13.5) | 3.0 g. |
| 8-5 | POE (40) octyl phenyl ether | (18.7) | 1.0 g. |
| 8-6 | POE (20) sorbitan monooleate | (15.0) | 3.0 g. |

Each of the analytical elements obtained by Examples 7 and 8 was cut into a piece 15 mm square and put in a plastic mount (disclosed in Japanese Patent Provisional Publication No. 57(1982)-63452) to prepare a slide for the analysis of GGT.

10 μl of each of control solution having protein content of 4% and 12% and GGT activity of 580 U/L was deposited (dropped) on each slide, and the color density thereof was measured after 2 and 5 minutes. The results are shown in Table 6. In Table 6, OD is the difference of values measured after 2 and 5 minutes.

TABLE 6

| Analytical Slide | OD (12%)/OD (4%) |
|---|---|
| Example 7 | 95% |
| Example 8-1 | 97% |
| Example 8-2 | 96% |
| Example 8-3 | 92% |
| Example 8-4 | 98% |
| Example 8-5 | 95% |
| Example 8-6 | 97% |

It is apparent from the above results that analytical elements using nonionic surfactant in addition to cationic surfactant have the improved spreadability of the spreading layer and that values measured by such elements are almost not interferred by protein content in sample solution.

We claim:

1. A reagent sheet for the measurement of the activity of γ-glutamyl transferase, comprising a porous sheet containing a substrate selected from the group consisting of γ-glutamyl-p-nitroanilide and γ-glutamyl-3-carboxy-4-nitroanilide, and a cationic surfactant in an amount ranging from 0.2 to 5 g/m².

2. The reagent sheet as claimed in claim 1, wherein said cationic surfactant is of a quaternary ammonium salt type.

3. The reagent sheet as claimed in claim 1, wherein said cationic surfactant is a compound having the formula:

$$n(R^1-R^5-\underset{\underset{R^3}{|}}{\overset{\overset{R^4}{|}}{N}}-R^2)^+ \cdot X^{n-}$$

wherein n is 1 or 2; $R^1$ is an alkyl group having 12 or more carbon atoms; $R^2$, $R^3$ and $R^4$ are the same or different from each other, and each is a methyl, ethyl or benzyl group, or $R^2$, $R^3$ and $R^4$ may form a piperidinium group together with the neighboring nitrogen atom; $R^5$ is a single bond or the group —$CONHR^6$— wherein $R^6$ is a methylene or ethylene group; and X is a halogen ion, sulfate ion or methansulfonate ion.

4. The reagent sheet as claimed in claim 1, wherein said reagent sheet contains a hydrophilic polymer.

5. The reagent sheet as claimed in claim 1, wherein said reagent sheet contains a cellulose derivative.

6. The reagent sheet as claimed in claim 1, wherein said reagent sheet contains a hydrophilic polymer in an amount ranging from 0.5 to 15 g./m².

7. An integral multilayer analytical element for the measurement of the activity of γ-glutamyl transferase, comprising a porous spreading layer containing a substrate selected from the group consisting of γ-glutamyl-p-nitroanilide and γ-glutamyl-3carboxy-4-nitroanilide and a cationic surfactant in an amount ranging from 0.2 to 5 g/m², a water-absorbing layer and a support layer in a laminated form.

8. The integral multilayer analytical element as claimed in claim 7, wherein said cationic surfactant is of a quaternary ammonium salt type.

9. The integral multilayer analytical element as claimed in claim 7, wherein said cationic surfactant is a compound having the formula:

$$n(R^1-R^5-\underset{\underset{R^3}{|}}{\overset{\overset{R^4}{|}}{N}}-R^2)^+ \cdot X^{n-}$$

wherein n is 1 or 2; $R^1$ is an alkyl group having 12 or more carbon atoms; $R^2$, $R^3$ and $R^4$ are the same or different from each other, and each is a methyl, ethyl or benzyl group, or $R^2$, $R^3$ and $R^4$ may form a piperidinium group together with the neighboring nitrogen atom; $R^5$ is a single bond or a group of —$CONHR^6$— wherein $R^6$ is methylene or ethylene group; and X is a halogen ion, sulfate ion or methanesulfonate ion.

10. The integral multilayer analytical element as claimed in claim 7, wherein said porous spreading layer contains a nonionic surfactant.

11. The integral multilayer analytical element as claimed in claim 7, wherein said porous spreading layer contains a nonionic surfactant having HLB value of 10 or more.

12. The integral multilayer analytical element as claimed in claim 7, wherein said porous spreading layer contains a nonionic surfactant in an amount of ranging from 0.1 to 3 g./m².

13. The integral multilayer analytical element as claimed in claim 7, wherein said porous spreading layer contains a hydrophilic polymer.

14. The integral multilayer analytical element as claimed in claim 7, wherein said porous spreading layer contains is a cellulose derivative.

15. The integral multilayer analytical element as claimed in claim 7, wherein said porous spreading layer contains a hydrophilic polymer in an amount ranging from 0.5 to 15 g./m².

* * * * *